US010373715B2

(12) United States Patent
Still et al.

(10) Patent No.: US 10,373,715 B2
(45) Date of Patent: Aug. 6, 2019

(54) TOOL AND METHOD FOR CONTROLLING THE SAME

(71) Applicant: MAKO Surgical Corp., Ft. Lauderdale, FL (US)

(72) Inventors: Stephen Eugene Still, Lake Worth, FL (US); Renbin Zhou, Wellington, FL (US)

(73) Assignee: MAKO SURGICAL CORP., Ft. Lauderdale, FL (US)

( * ) Notice: Subject to any disclaimer, the term of this patent is extended or adjusted under 35 U.S.C. 154(b) by 326 days.

(21) Appl. No.: 15/289,599

(22) Filed: Oct. 10, 2016

(65) Prior Publication Data

US 2017/0109488 A1    Apr. 20, 2017

Related U.S. Application Data

(60) Provisional application No. 62/242,535, filed on Oct. 16, 2015.

(51) Int. Cl.
*G05D 23/00* (2006.01)
*G16H 40/63* (2018.01)
(Continued)

(52) U.S. Cl.
CPC ....... *G16H 40/63* (2018.01); *A61B 17/32002* (2013.01); *A61B 34/30* (2016.02);
(Continued)

(58) Field of Classification Search
CPC ....... G01R 33/07; A61B 34/71; A61B 17/068; A61B 17/1626; A61B 17/151;
(Continued)

(56) References Cited

U.S. PATENT DOCUMENTS 5,747,953 A * 5/1998 Philipp .............. A61B 17/1626
                                                        318/114
5,872,852 A    2/1999 Dougherty
(Continued)

FOREIGN PATENT DOCUMENTS

EP        2508141 A1    10/2012
JP    2000011827 A     1/2000
(Continued)

OTHER PUBLICATIONS

JP4879570 B2 English language translation; Downloaded espace.net on Jan. 10, 2017; 26 pages.
(Continued)

*Primary Examiner* — Tuan A Vu
(74) *Attorney, Agent, or Firm* — Howard & Howard Attorneys PLLC (57) ABSTRACT

A tool and method for operating the tool are provided. The tool includes a housing and a power generator, such as a motor, disposed in the housing. The power generator has an operating parameter, such as rotational speed. A trigger member and associated magnet are displaceable relative to the housing. A plurality of sensors each generate an output signal based on movement of the magnet. A controller receives the output signals from the sensors, determines a base digital integer from each of the output signals, concatenates the base digital integers to form a concatenated digital integer. The controller varies the operating parameter based on the concatenated digital integer.

17 Claims, 7 Drawing Sheets

(51) Int. Cl.
*H03K 17/97* (2006.01)
*A61B 34/30* (2016.01)
*G05B 19/402* (2006.01)
*A61B 17/32* (2006.01)
*G01D 5/14* (2006.01)
*A61B 17/00* (2006.01)

(52) U.S. Cl.
CPC ............ *G05B 19/402* (2013.01); *H03K 17/97* (2013.01); *A61B 2017/00017* (2013.01); *A61B 2017/00367* (2013.01); *A61B 2017/00398* (2013.01); *G01D 5/145* (2013.01); *G05B 2219/45169* (2013.01); *G05B 2219/49272* (2013.01)

(58) Field of Classification Search
CPC ........ G01D 5/145; G01D 5/20; H02P 7/2913; B64D 2027/026; G16H 40/63
See application file for complete search history.

(56) References Cited

U.S. PATENT DOCUMENTS

| | | | | |
|---|---|---|---|---|
| 6,017,354 | A * | 1/2000 | Culp | A61B 17/1626 604/22 |
| 6,025,683 | A * | 2/2000 | Philipp | H02P 7/2913 318/139 |
| 7,221,151 | B2 | 5/2007 | Schroeder et al. | |
| 8,010,180 | B2 | 8/2011 | Quaid et al. | |
| 9,046,383 | B2 | 6/2015 | Friedrich et al. | |
| 2007/0085496 | A1 * | 4/2007 | Philipp | A61B 17/151 318/139 |
| 2008/0042644 | A1 | 2/2008 | Heo et al. | |
| 2009/0091448 | A1 | 4/2009 | Leyden et al. | |
| 2013/0172903 | A1 | 7/2013 | Suarez et al. | |
| 2014/0070796 | A1 * | 3/2014 | Reymond | G01D 5/145 324/207.2 |
| 2014/0145714 | A1 * | 5/2014 | Okatake | G01R 33/07 324/225 |
| 2014/0246471 | A1 * | 9/2014 | Jaworek | A61B 17/068 227/175.1 |
| 2014/0345408 | A1 | 11/2014 | Pfeifer et al. | |
| 2015/0050013 | A1 | 2/2015 | Cadugan et al. | |
| 2015/0088161 | A1 * | 3/2015 | Hata | A61B 34/71 606/130 |
| 2015/0272571 | A1 | 10/2015 | Leimbach et al. | |
| 2016/0169706 | A1 * | 6/2016 | Kejik | G01D 5/20 324/207.25 |

FOREIGN PATENT DOCUMENTS

| | | |
|---|---|---|
| JP | 2009222594 A | 10/2009 |
| JP | 4879570 B2 | 2/2012 |
| WO | 2014153665 A1 | 10/2014 |
| WO | 2015007540 A1 | 1/2015 |

OTHER PUBLICATIONS

JP2000011827 A English language translation; Downloaded espace. net on Jan. 11, 2017; 27 pages.
English language abstract and machine-assisted English translation for JP 2009-222594 extracted from espacenet.com database on Dec. 3, 2018, 43 pages.
Honeywell, "Hall Effect Sensing and Application Manual", 2015, pp. 1-76.
Mathworks, "Vector Concatenate", Dec. 2017, https://mathworks.com/help/simulink/slref/vectorconcatenate.html, 5 pages.

\* cited by examiner

TOOL AND METHOD FOR CONTROLLING THE SAME

CROSS-REFERENCE TO RELATED APPLICATION

The subject application claims the benefit of U.S. Provisional Patent Application No. 62/242,535, filed on Oct. 16, 2015, the disclosure of which is hereby incorporated by reference in its entirety.

TECHNICAL FIELD

The embodiments described herein relate to a tool and method for controlling the tool.

BACKGROUND

In the medical field, surgical tools take many forms. In some cases, the tools are powered to perform surgical procedures. Such tools can include motorized surgical drills, burs, saws, reamers, and the like. The surgeon regulates a speed of the tool using a trigger member. Prior art methods for controlling the speed of the tool utilize a magnet and one or more Hall Effect sensors to measure a displacement of the trigger member. For example, Japanese patent JP 4879570B2 discloses a power tool with a magnet linked to a trigger member and two Hall Effect sensors to control a speed of the power tool.

Typically, tools used in surgical procedures are reusable, but need to be sterilized before each use. Some sterilization techniques can be harsh on components of the tool such as the magnet and/or the Hall Effect sensors. High temperatures involved in autoclave sterilization may cause degradation of such components. Such degradation may cause variations in the measurements of the displacement of the trigger member, potentially resulting in incorrect speeds of the tool, or the inability of the tool to reach a maximum speed. There remains an opportunity to address at least the aforementioned problems.

SUMMARY

One embodiment of a tool is provided. The tool comprises a housing and a power generator disposed in the housing and having an operating parameter. The tool comprises a trigger member displaceable relative to the housing. A magnet is coupled to the trigger member such that displacement of the trigger member results in movement of the magnet. A plurality of sensors are disposed in the housing and located adjacent to the magnet. Each sensor is configured to generate an output signal in response to detecting the magnet upon displacement of the trigger member. A controller is coupled to the sensors and is configured to receive the output signals. The controller determines a base digital integer from each of the output signals, concatenates the base digital integers to form a concatenated digital integer, and varies the operating parameter based on a value of the concatenated digital integer.

One embodiment of a method for operating a tool is provided. The tool has a housing and a power generator disposed in the housing and having an operating parameter. A trigger member is displaceable relative to the housing and a magnet is coupled to the trigger member. A plurality of sensors are located adjacent to the magnet and are disposed in the housing. A controller is coupled to the sensors. The method comprises moving the magnet by displacing the trigger member, detecting the magnet with the sensors, and generating an output signal from each sensor in response to detecting the magnet. The controller receives the output signal from each sensor and determines a base digital integer from each of the output signals. The controller concatenates the base digital integers to form a concatenated digital integer. The controller varies the operating parameter based on a value of the concatenated digital integer.

One embodiment of a method for controlling a surgical tool is provided. The tool comprises a power generator, a displaceable magnet, and a plurality of sensors located adjacent to the magnet. A controller is coupled to the sensors and the power generator. The method comprises the controller performing the steps of receiving an output signal from each sensor in response to detecting the magnet, determining a base digital integer from each of the output signals, concatenating the base digital integers to form a concatenated digital integer, and varying operation of the power generator based on the concatenated digital integer.

The tool and method respectively provide components and techniques whereby the negative effects of sterilization on components of the tool, such as the magnet and/or the sensors, are mitigated. Even if degradation occurs to any of the components, the potential for malfunctioning of the tool is reduced because the operating parameter is varied based on the concatenated digital integer, which is the combination from the relative sensor measurements i.e., the base digital integer from each of the output signals. The tool and method may exhibit other advantages other than those described herein.

BRIEF DESCRIPTION OF THE DRAWINGS

Advantages of the present invention will be readily appreciated as the same becomes better understood by reference to the following detailed description when considered in connection with the accompanying drawings wherein.

DETAILED DESCRIPTION

Figure 1A:
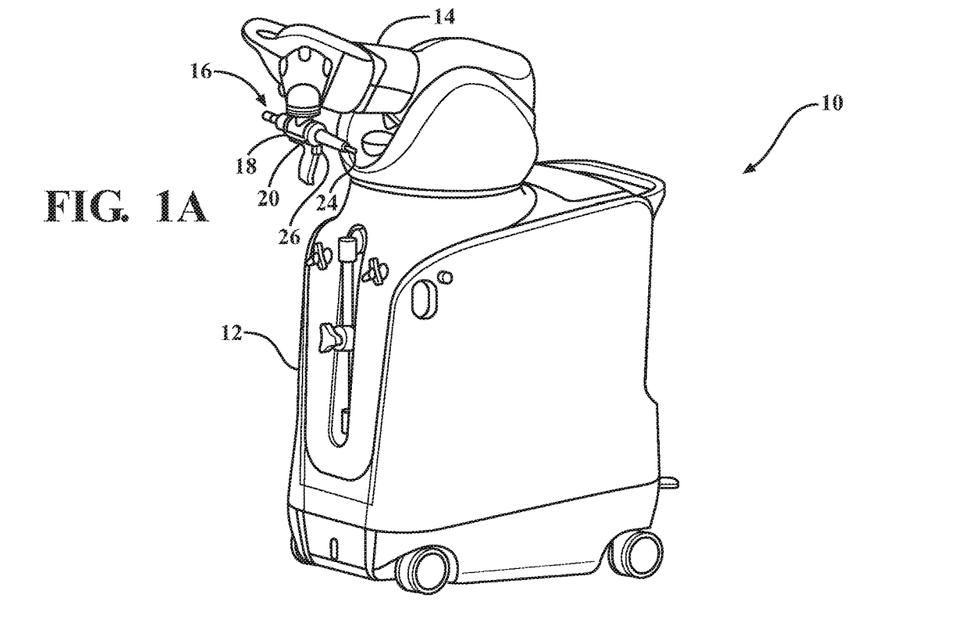
FIG. 1A is a perspective view of a robotic system showing a tool at a distal end of an arm coupled to a base.
Figure 1B:
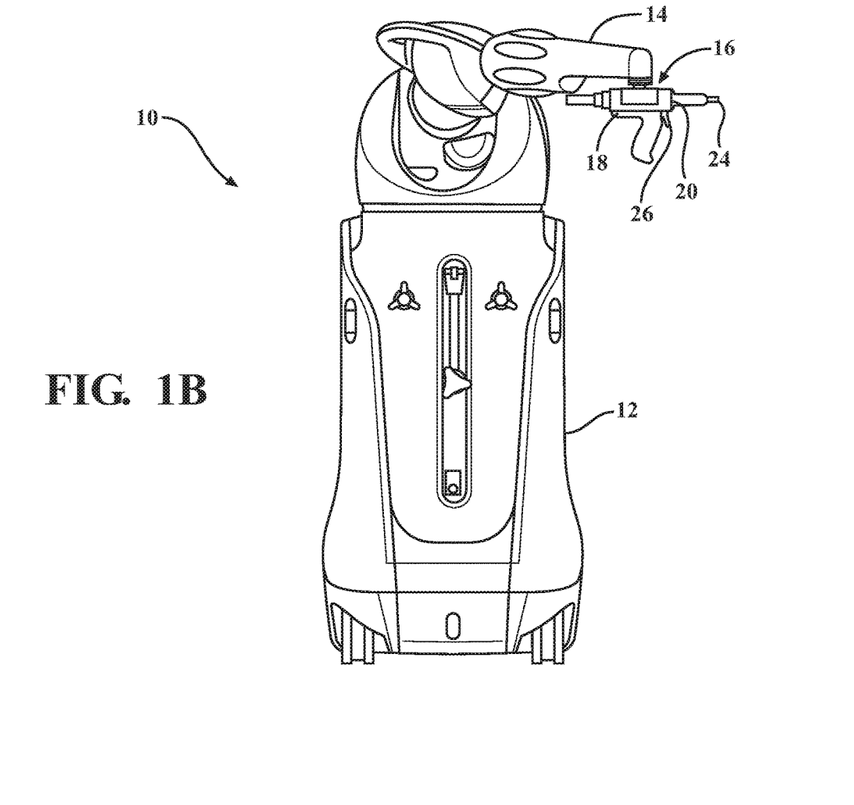
FIG. 1B is another perspective view of the robotic system of FIG. 1A showing the tool at the distal end of the arm coupled to the base.

Referring to the Figures, wherein like numerals indicate like or corresponding parts throughout the several views, a robotic system is shown generally at 10 in FIGS. 1A and 1B. In one example, the robotic system 10 has a base 12, an arm 14, and an end effector 16. The base 12 is mobile allowing transportation to different operating rooms as necessary. The arm 14 is a robotic arm and is moveably attached to the base 12. The arm 14 assists the user during a surgical procedure by supporting and aligning the end effector 16. The arm 14 reduces user fatigue and error by supporting the end effector 16 while in use, as well as restricting movement that is outside of a predetermined range. One such arm is disclosed in U.S. Pat. No. 8,010,180, the disclosure of which is hereby incorporated herein by reference.

Figure 2:
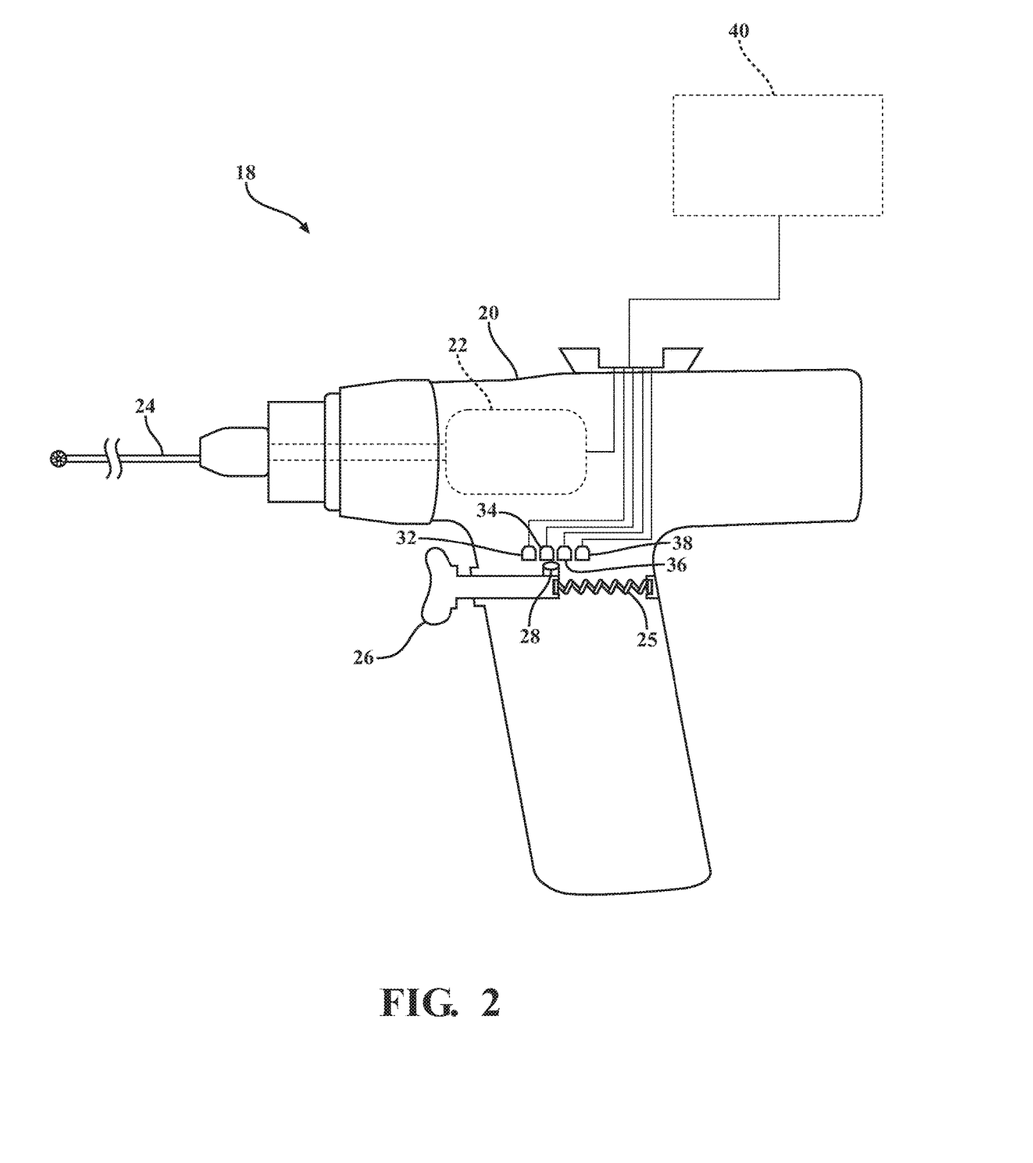
FIG. 2 is a schematic representation of the tool as shown in FIGS. 1A and 1B according to one embodiment.

The end effector 16 comprises a tool 18 operable by the user. The tool 18 is schematically illustrated in FIG. 2. When utilized in the robotic system 10, the tool 18 is operable with and supported by the arm 14. Alternatively, the tool 18 may be hand-held such that the tool 18 is supported by a hand and arm of the user. The tool 18 aids in surgical procedures by cutting, shaping, cauterizing, and/or reaming tissue, such as bone.

As shown in FIG. 2, the tool 18 includes a housing 20 for enclosing components of the tool 18. A power generator 22 is disposed in the housing 20. The power generator 22 may include a motor, an ultrasonic generator, or any other suitable transducer for converting electrical energy into mechanical energy. In one embodiment, the power generator 22 is a 3-phase brushless DC motor. Operation of the power generator 22 is defined by an operating parameter. In other words, the power generator 22 operates by and/or is controlled according to the operating parameter. Possible operating parameters include rotational speed (RPM), frequency of commutation (Hz), amplitude of ultrasonic energy, or frequency of ultrasonic energy (Hz). Other operating parameters may be utilized depending on the configuration of the power generator 22. Additionally, the power generator 22 may be operated by and/or controlled according more than one operating parameter.

The tool 18 comprises an energy applicator 24. The energy applicator 24 is the component that applies the energy output by the power generator 22 to a patient during the surgical procedure. If the power generator 22 is a motor, the energy applicator 24 may be a drill, a saw blade such as a sagittal saw blade, or a bur coupled to a drive shaft or other drive mechanism of the motor. If the power generator 22 is an ultrasonic generator, the energy applicator 24 is an ultrasonic tip. If the power generator 22 outputs photonic energy, the energy applicator 24 is a member that is transparent to the wavelength of light emitted by the power generator 22. The energy applicator 24 extends outward from the housing 20, and may do so according to any suitable direction depending on its configuration. The tool 18 may comprise any other energy applicator 24 for interacting with the patient other than those described herein.

Figure 3A:
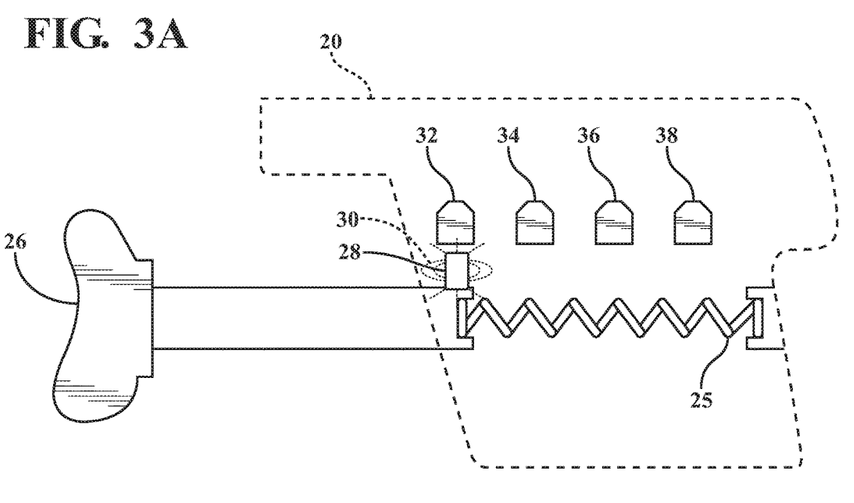
FIG. 3A is an illustration of a trigger member in a first position according to one embodiment.
Figure 3B:
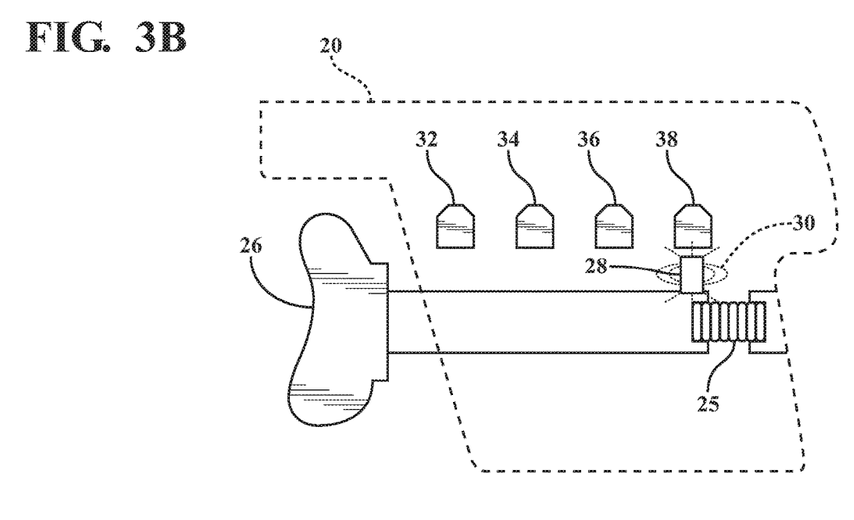
FIG. 3B is an illustration of the trigger member in a second position according to one embodiment.

The tool 18 also comprises a trigger member 26 that is displaceable relative to the housing 20 between an initial, unactuated position (e.g., FIG. 3A) and a fully-depressed position (e.g., FIG. 3B). The trigger member 26 is slidably coupled to the housing 20 and is configured to move along a predetermined path of movement. The trigger member 26, as shown in the figures, moves horizontally and linearly. However, it is to be appreciated that the trigger member 26 may be displaceable according to various other configurations, such as vertically, rotationally (about a pivot), or the like.

A magnet 28 is coupled to the trigger member 26. The trigger member 26 is configured to move the magnet 28 such that displacement of the trigger member 26 results in movement of the magnet 28. The magnet 28 may be any type of device capable of generating a magnetic field 30 or an electromagnetic field. The magnet 28 may be a passive device that is not electrically energized, such as a permanent magnet. Alternatively, the magnet 28 may be an active device that is electrically energized, such as electromagnet. The magnet 28 may further be made from a variety of materials including, but not limited to Neodymium, Ferrite, and Samarium. The magnet 28 may be attached to the trigger member 26 according to any suitable technique or means, such as by adhesive, by being placed in a magnet holder, or the like. The magnet 28 shown is fixed to the trigger member 26.

In some embodiment, such as shown in FIGS. 3A and 3B, a biasing device 25, is disposed between the trigger member 26 and the housing 20 to return the trigger member 26 to its initial, unactuated position during operation. In the embodiment shown, the trigger member 26 slides in a bore in the housing 20 against the bias of the biasing device 25 when actuated by the user.

The biasing device 25 may be a passive or active device. When the biasing member 25 is a spring, the biasing member 25 may be a compressing spring, extension spring, torsion spring, or the like. When active, the biasing member 25 may be implemented by any suitable actuator, such as electrical or pneumatic actuators, or the like.

Referring to FIGS. 2, 3A, and 3B, the tool 18 comprises a plurality of sensors 32, 34, 36, 38. The tool 18 may include any suitable number of sensors 32, 34, 36, 38 other than those shown in the Figures. The sensors 32, 34, 36, 38 are mounted inside the housing 20. The sensors 32, 34, 36, 38 are generally fixed from moving relative to the housing 20. The sensors 32, 34, 36, 38 are located adjacent to the magnet 28 when the magnet 28 slides with the trigger member 26 between the initial, unactuated position and the fully-depressed position. That is, the sensors 32, 34, 36, 38 are generally located along the path of movement of the magnet 28. The sensors 32, 34, 36, 38 are generally in a non-contact or spaced relationship to the magnet 28 such that detection of the magnet 28 occurs through an air gap between each sensor 32, 34, 36, 38 and the magnet 28. The sensors 32, 34, 36, 38 may be disposed on a printed circuit board (not shown) mounted to or inside the housing 20. According to one embodiment, the plurality of sensors includes a first sensor 32, intermediate (middle) sensors 34, 36, and a last sensor 38. By way of non-limiting example, the sensors 32, 34, 36, 38 may be Hall Effect, magnetoresistive (such as Anisotropic magnetoresistive (AMR) or Tunnel magnetoresistive (TMR)), and fluxgate types. Moreover, more than one magnet 28 may be utilized by the tool 18 depending on the specific implementation.

The plurality of sensors 32, 34, 36, 38 may be any type of sensor capable of generating output signals corresponding to position or orientation of the magnet 30 and/or the strength of the magnetic field 30 produced by the magnet 28. In general, the output signal generated by each sensor 32, 34, 36, 38 is dependent on a spatial relationship (e.g. displacement, orientation, etc.) between the magnet 28 and each respective sensor 32, 34, 36, 38. The spatial relationship between the magnet 28 and each respective sensor 32, 34, 36, 38 causes changes in the strength of the magnetic field 30 detected by each sensor 32, 34, 36, 38. The output signals generated by the plurality of sensors 32, 34, 36, 38 may be a digital or analog representation of electric current flow, voltage potential, resistance, or the like.

It should be appreciated that not every single sensor 32, 34, 36, 38 present in the tool 18 may generate an output signal. In some instances, depending on the configurations of the sensors 32, 34, 36, 38, the trigger member 26 and magnet 28, and paths of movement thereof, only certain sensors 32, 34, 36, 38, and not others, may generate the output signals. However, it is generally understood that more than one sensor 32, 34, 36, 38 should generate the output signals to implement the techniques described herein.

Figure 6:
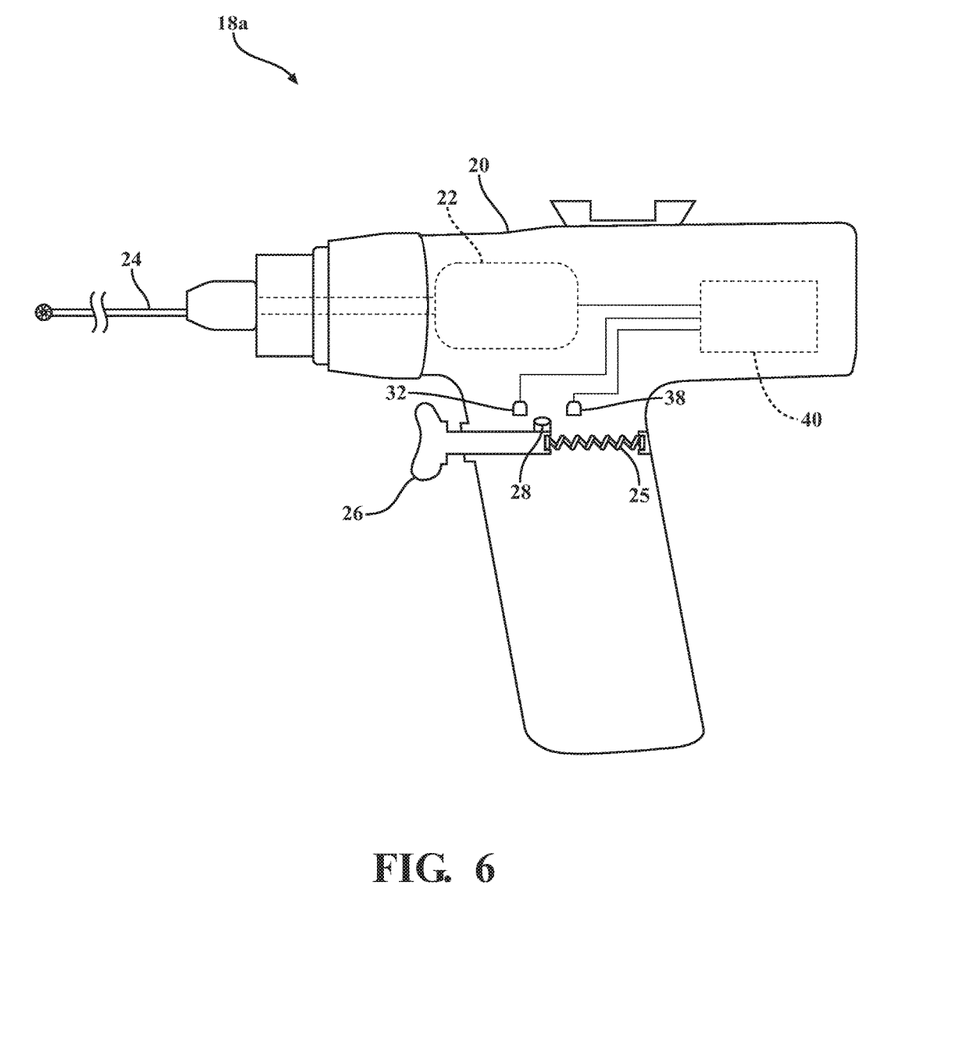
FIG. 6 is a layout of the tool according to another embodiment.

A controller 40 is coupled to the sensors 32, 34, 36, 38 to receive each of the output signals. In one embodiment, as shown in FIG. 6, the controller 40 is mounted within the housing 20. For example, the controller 40 may be mounted to the same printed circuit board as the sensors 32, 34, 36, 38. Alternatively, as shown in FIG. 2, the controller 40 may be mounted in a component separate from the tool 18 or housing 20. For example, the controller 40 may be integrated into the base 12, arm 14, or other parts of the end effector 16 of the robotic system 10.

The controller 40 has one or more microprocessors for processing instructions. The controller 40 further includes memory for storing instructions to be processed. Additionally or alternatively, the controller 40 may comprise one or more microcontrollers, field programmable gate arrays, systems on a chip, discrete circuitry, and/or other suitable hardware, software, or firmware that is capable of carrying out the functions described herein.

The controller 40 is further coupled to the power generator 22 to control the power generator 22. Based on the output signals, the controller 40 induces the power generator 22 to operate at a value of the operating parameter. The value of the operating parameter generally relates to displacement of the trigger member 26. However, as will be described below, advanced techniques are provided to determine the operating parameter.

Figure 4A:
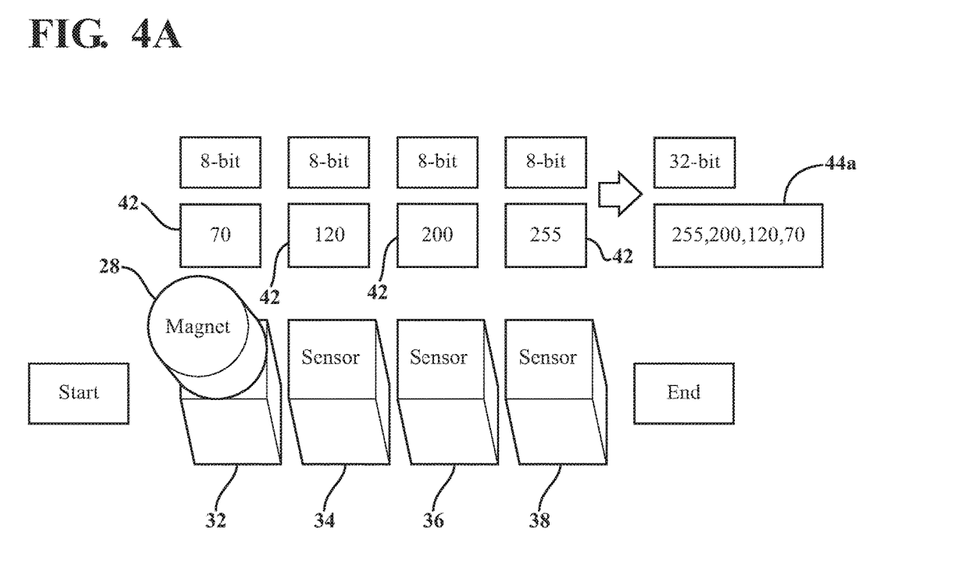
FIG. 4A is an illustration showing a magnet and sensors of the tool in a first example wherein corresponding base digital integers from each sensor and a concatenated digital integer for varying operation of the tool are determined according to one embodiment.
Figure 4B:
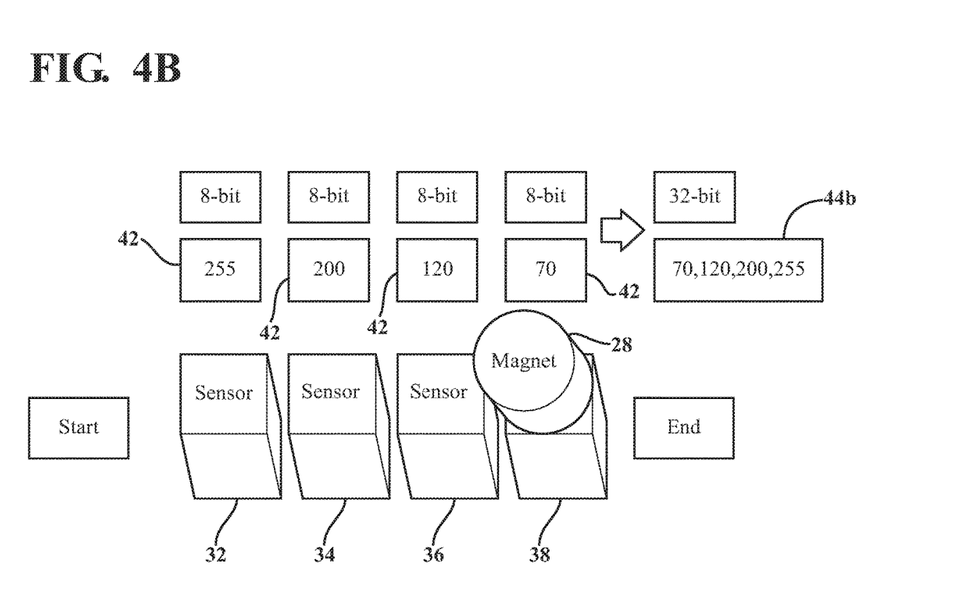
FIG. 4B is an illustration showing the magnet and sensors of the tool in a second example wherein corresponding base digital integers from each sensor and the concatenated digital integer for varying operation of the tool are determined according to one embodiment.

Referring to FIGS. 4A and 4B, the controller 40 determines base digital integers 42 from each of the output signals during operation. In the embodiment shown, the sensors 32, 34, 36, 38 are Hall Effect sensors configured to generate an analog output signal of from 0-5 volts. The controller 40 performs an analog-to-digital quantization of the output signals from each of the sensors 32, 34, 36, 38. Using such quantization, the controller 40 samples and converts analog output signal as a function of time into a discrete-time signal. The quantization process creates the base digital integers 42 derived from the output signals. The base digital integers 42 may be stored in memory device accessible by the controller 40.

Each base digital integer 42 is further defined as an N-bit digital integer. Here, N is a bit resolution (bit depth or bit size) of each sensor 32, 34, 36, 38. When the controller 40 determines the base digital integer 42, it does so by determining an integer from any one of $2^N$ values. In the embodiment shown, the base digital integers 42 are an 8-bit digital number which has $2^8$ possible values which range from 0-255. The base digital integers 42 indicate the strength of the magnetic field 30, which varies as a function of distance from the magnet 28, i.e. each base digital integer 42 effectively relates to the relationship between each sensor 32, 34, 36, 38 and the magnet 28.

The magnet 28 may exhibit various patterns of magnetic fields 30 depending on the configuration of the magnet 28. Such variations may exist on many factors, such as depending on whether a south or north pole of the magnet 28 is arranged to face the sensors 32, 34, 36, 38. Depending on the arrangement of the magnet 28, the output signals from the sensors 32, 34, 36, 38 may be either greater than a midpoint value or less than the midpoint value. For instance, the sensors 32, 34, 36, 38 may be configured to generate an analog signal of 2.5 volts in the absence of any magnetic field 30 from the magnet 28, but generate an analog signal from 2.5-5.0 volts in one installation of the magnet 28 or from 0.0-2.5 volts in another installation of the magnet 28.

The controller 40 determines the base digital integers 42 in the manner described above, but in one installation of the magnet 28 (e.g., south facing) the base digital integers 42 range from 0-255, while in the other installation of the magnet 28 (e.g., north facing) the base digital integers 42 range from 256-511. In the latter case, the values of the base digital integer 42 are automatically converted by the controller 40 to range from 0-255. In other words, the controller 40 automatically accommodates either installation of the magnet 28, i.e., either south pole facing or north pole facing. Furthermore, since the magnet 28 can be installed in either polarity direction, the tool 18 is easier to build.

It is to be appreciated that the value of the base digital integer 42 may be directly, inversely, positively or negatively correlated with the relationship between each sensor 32, 34, 36, 38 and the magnet 28. For example, as shown in FIGS. 4A and 4B, the closer the magnet 28 is to a sensor, the lesser the base digital integer 42, while the further the magnet 28 is to a sensor, the greater base digital integer 42. Depending on the configuration of the magnet 28 and the sensors 32, 34, 36, 38, such correlations may be perfect, near perfect, or somewhat weak.

The controller 40 concatenates the base digital integers 42 to form a concatenated digital integer 44. Values of the concatenated digital integer 44 are used to relate measurements from one of the sensors 32, 34, 36, 38 to measurements of the other sensors. By concatenation, the controller 40 combines the base digital integers 42 end-to-end to form the concatenated digital integer 44. The concatenated digital integer 44 is a combination of the base digital integers 42 to form a single digital concatenated integer. The controller 40 may perform this concatenation starting from the base digital integer 42 from the first sensor 32 and ending with the base digital integer 42 from the last sensor 38. Alternatively, as shown in FIGS. 4A and 4B, the controller 40 may concatenate starting from the base digital integer 42 from the last sensor 38 and ending with the base digital integer 42 from the first sensor 32. In other embodiments, the controller 40 may concatenate the base digital integers 42 in according to other orders or directions depending on, for example, the way the controller 40 is coupled to the sensors 32, 34, 36, 38, the position of the magnet 28, the nature of the concatenation, or the like. In FIGS. 4A, and 4B, the concatenated digital integer 44 is illustrated having the base digital integers 42 separated by commas for simplicity in understanding the source of the base digital integers 42. The concatenated digital integer 44 may be formed without presence of such commas.

In one embodiment, S is a total number of sensors 32, 34, 36, 38 that generate the output signals and the concatenated digital integer 44 is defined as an M-bit digital integer. Here, M is a bit resolution (bit depth or bit size) of the concatenated digital integer 44 with M=S*N. The controller 40 may determine the concatenated digital integer 44 to be any one of $2^M$ values. In the embodiment shown in FIGS. 4A and 4B, S=4 such that four sensors 32, 34, 36, 38 generate the output signals, N=8 for each sensor 32, 34, 36, 38 such that the bit resolution of each sensor is 8-bits and M=32 such that the bit resolution of the concatenated digital integer 44 is 32-bits. As such, the concatenated digital integer 44 is a 32-bit digital number which has $2^{32}$ possible values.

The controller 40 may perform any suitable conversion to the base digital integers 42 to form the concatenated digital integer 44. For instance, the base digital integers 42, ranging from 0-255 (in decimal), can be converted from decimal to binary and then concatenated to form a 32-bit binary number, which can then be converted back to decimal to yield the concatenated digital integer 44.

The controller 40 utilizes the concatenated digital integer 44 for controlling the power generator 22. The controller 40 varies the value of the operating parameter based on the value of the concatenated digital integer 44. For example, the controller 40 induces the power generator 22 to generate energy at a rate, frequency, level, or any other unit which related to or corresponding to the value of the concatenated digital integer 44. The value of the concatenated digital integer 44 may be may be directly, inversely, positively or negatively correlated with the value of the operating parameter.

Figure 5:
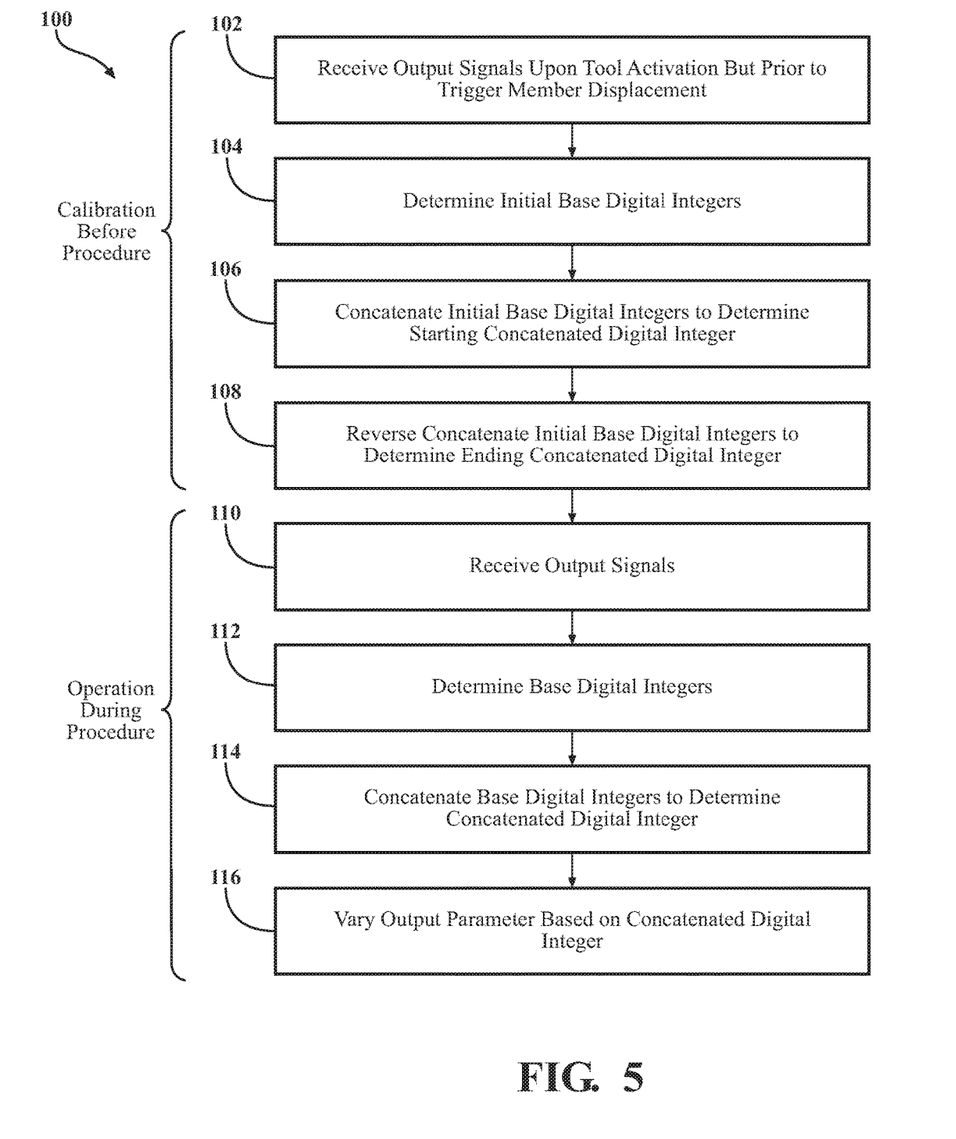
FIG. 5 is a flow diagram of a method for operating the tool according to one embodiment.

A method for operating the tool 18 is shown generally at 100 in FIG. 5. For simplicity, the method may be segmented into a first part for calibrating the tool 18 and including steps 102, 104, 106, and 108 and a second part for controlling the tool 18 during a surgical procedure, including steps 110, 112, 114 and 16.

The method includes the step of the user activating the tool 18. In step 102, upon activation of the tool 18, and prior to displacement of the trigger member 26, output signals from the plurality of sensors 32, 34, 36, 38 are received by the controller 104. When the user activates the tool 18 the trigger member 26 has zero displacement.

In step 104 the controller 40 determines initial base digital integers 42 from each of the output signals with the trigger member 26 in the initial, unactuated position. Each initial base digital integers 42 relates to the spatial relationship between each sensor 32, 34, 36, 38 and the magnet 28 when the trigger member 26 is in the initial, unactuated position. Subsequently, the controller 40 concatenates the initial base digital integers 42 in step 106 to form a starting concatenated digital integer 44a (See FIG. 4A). More specifically, the controller 40 assigns values of the initial base digital integers 42 to determine the starting concatenated digital integer 44a. In step 108, the controller 40 assigns values of the initial base digital integers 42 to determine an ending concatenated digital integer 44b (See FIG. 4B). More specifically, using the values of the initial base digital integers 42, the ending concatenated digital integer 44b is determined by concatenating in reverse order of the starting concatenated digital integer 44a. The ending concatenated digital integer 44b establishes a predicted position of the magnet 28 in which the displacement of the trigger member 26 is a maximum. Thus, in this embodiment, the magnet 28 need not be displaced to the last sensor 38 to determine the ending concatenated digital integer 44b. The starting and ending concatenated digital integers 44b represent endpoints of the displacement of the trigger member 26. In this way the concatenated digital integers 44 determined during operation further represent relative displacement of the trigger member 26 over a stroke bounded by the initial, unactuated position and the fully-depressed position, e.g., a starting and ending position. The starting and ending positions of the trigger member 26 are defined according to displacement when the magnet 28 is nearest the first and last sensors 32, 38.

An operating range bounded by minimum and maximum values of the operating parameter can be assigned to the endpoints of displacement of the trigger member 26. By assigning the starting concatenated digital integer 44a and the ending concatenated digital integer 44b, respectively, to minimum and maximum values of the operating parameter, effects of magnet strength degradation may be mitigated. If the magnet 28 becomes degraded over time such that the range of the base digital integers 42 is reduced, the tool 18 will still operate as designed because the relative displacement of the trigger member 26 is determined as opposed to an absolute displacement.

The user can operate the tool 18 once the starting concatenated digital integer 44a and the ending concatenated digital integer 44b are assigned to the minimum and maximum displacement of the trigger member 26. The user operates the tool 18 by holding the trigger member 26 at a desired displacement. When the user pauses during the surgical procedure or completes the surgical procedure, the trigger member 26 is released allowing the displacement to return to the initial, unactuated position.

In the second part of the method, and at step 110, the controller 40 receives the output signals from each of the sensors 32, 34, 36, 38 during the surgical procedure. The controller 40 determines the base digital integers 42 from the output signals at step 112, during the surgical procedure. Subsequently, the base digital integers 42 are concatenated to form the concatenated digital integer 44 at step 114 during the surgical procedure. The controller 40 varies the operating parameter in step 116 based on values of the concatenated digital integer 44. The controller 40 induces the power generator 22 to operate at a desired value of the operating parameter. All values of the operating parameter over the operating range are able to be controlled in this method. For example, if the tool 18 is a drill, zero displacement of the trigger member 26 is the initial, unactuated position indicating "OFF" or 0 rpm rotational speed of the energy applicator 24. Displacing the trigger member 26 starts rotation of the energy applicator 24 at a rate corresponding to displacement of the trigger member 26. Maximum rotational speed of the energy applicator 24 could be achieved when the trigger member 26 is in the fully-depressed position.

The tool 18 is configured to continue operation even if there is a failure of any of the sensors 32, 34, 36, 38. When the controller 40 detects a failure in one of the sensors 32, 34, 36, 38, the value of the base digital integer 42 associated with the failed sensor(s) is ignored. Relative displacement of the trigger member 26 with respect to the three remaining sensors is still determinable. This allows the user to continue to operate the tool 18 during the surgical procedure.

A failure of greater than two sensors may also be overcome if one of either the first sensor 32 or the last sensor 38 is still operational and the magnet 28 is limited from moving past a range of the operational sensor 32 or 38 (i.e., the operational sensor will not produce identical readings at different trigger positions). In such a case, as only one sensor 32 or 38 is operational, the controller 40 reverts to conventional methods of varying the operating parameter. For example, the operating parameter is varied based on concatenated digital integer 44 derived from the output signal of the operational sensor 32 or 38.

In alternative embodiments, the magnet 28 is held fixed to the housing 20, while the sensors 32, 34, 36, 38 are mounted to the trigger member 26 to move with the trigger member 26 relative to the magnet 28 upon displacement by the user. The same techniques applied above relating to varying the output parameter may be equally applied to this alternative embodiment.

Another embodiment of the tool 18a is shown generally in FIG. 6. In this embodiment, the trigger member 26 is displaceable such that the magnet 28 moves between the first sensor 32 and the last sensor 38, i.e., the intermediate sensors 34, 36 have been removed in this embodiment. In this embodiment, the first sensor 32 and the last sensor 38 essentially define start and end positions for the magnet 28, i.e., the magnet 28 is effectively bounded by the first sensor 32 and the last sensor 38 and moves therebetween. The magnet 28 need not extend completely to one or the other of the first sensor 32 and the last sensor 38 and is preferably spaced from each of the first sensor 32 and the last sensor 38 in the initial, unactuated position and the fully-depressed position, respectively.

Figure 7:
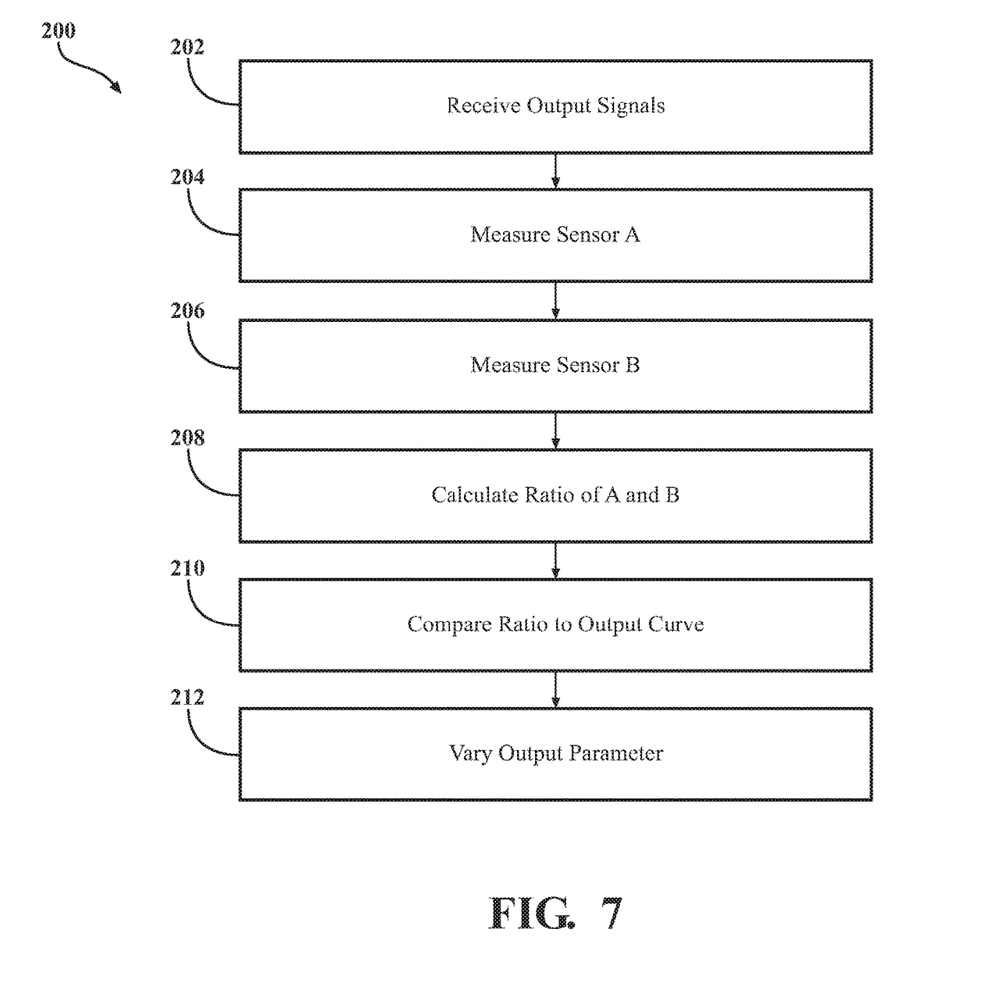
FIG. 7 is a flow diagram of a method for operating the tool according to another embodiment.

The second embodiment further includes a method for controlling the tool 18a shown generally at 200 in FIG. 7. A first step 202 comprises the controller 40 receiving output signals from the sensors 32, 38. The controller 40 then measures the output signal from the first sensor 32 in step 204. In step 206 the controller 40 measures the output signal from the last sensor 38. Using the measurements of the output signals the controller 40 calculates a ratio of the signals in step 208. The ratio is then compared to an output curve in step 210 to determine the value of the operating parameter. The output curve is a table that defines the operating parameter for a particular ratio. The value of the operating parameter is varied in step 212 along with the displacement of the trigger member 26. By determining the value of the operating parameter from the ratio of measurements taken from two sensors 32, 38, the effects of magnet strength degradation may be mitigated, i.e., by using relative sensor measurements. Such techniques may utilize the base digital integers 42, as described above.

The term "memory" is intended to comprise memory associated with a processor such as a CPU, and may include, for example, RAM (random access memory), ROM (read only memory), a fixed memory device (for example, hard drive), a removable memory device (for example, diskette), a flash memory, combinations thereof, and the like.

As will be appreciated by one skilled in the art, the embodiments described herein may include a computer program product embodied in one or more computer readable medium(s) having computer readable program code embodied thereon. Computer software including instructions or code for performing the methods described herein, may be stored in one or more of the associated memory devices (for example, ROM, fixed or removable memory) and, when ready to be utilized, is loaded in part or in whole (for example, into RAM) and implemented by a CPU. Such software could include, but is not limited to, firmware, resident software, microcode, and the like.

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

The invention claimed is:

1. A tool comprising:
a housing;
a power generator disposed in said housing and having an operating parameter;
a trigger member displaceable relative to said housing;
a magnet coupled to said trigger member such that displacement of said trigger member results in movement of said magnet;
a plurality of sensors disposed in said housing and located adjacent to said magnet, and each sensor being configured to generate an output signal in response to detecting said magnet upon displacement of said trigger member, wherein S is a total number of sensors that generate said output signals; and
a controller coupled to said sensors and being configured to:
receive said output signals,
determine a base digital integer from each of said output signals, wherein said base digital integer is further defined as an N-bit digital integer, wherein N is a bit resolution of each sensor wherein said base digital integer is any one of $2^N$ values,
concatenate said base digital integers to form a concatenated digital integer, wherein said concatenated digital integer is further defined as an M-bit digital integer, wherein M is a bit resolution of said concatenated digital integer with M=S*N and wherein said concatenated digital integer is any one of $2^M$ values, and
vary said operating parameter based on a value of said concatenated digital integer.

2. The tool of claim 1 wherein said sensors are arranged along a predetermined path of movement of said magnet and are each disposed in a spaced relationship relative to said magnet.

3. The tool of claim 1 wherein said magnet produces a magnetic field that is detectable by each sensor with the magnetic field being variable as a function of a spatial relationship between said magnet and each sensor and wherein said base digital integer is representative of a strength of the magnetic field detected by each sensor.

4. The tool of claim 1 wherein said controller is further configured to:
determine said base digital integer from each of said output signals after activating said tool and prior to trigger member displacement during which said trigger member has zero displacement;
concatenate said base digital integers to establish a first concatenated digital integer corresponding to a minimum of an operating range of said operating parameter; and
establish a second concatenated digital integer by reversing said first concatenated digital integer wherein said second concatenated digital integer corresponds to an estimated maximum of said operating range of said operating parameter.

5. The tool of claim 1 wherein S=4 such that four sensors generate said output signals, wherein N=8 for each sensor such that said bit resolution of each sensor is 8-bits and wherein M=32 such that said bit resolution of said concatenated digital integer is 32-bits.

6. The tool of claim 1 wherein said power generator is a motor and wherein said operating parameter is one or more of a rotational speed and a rotational frequency of said motor.

7. The tool of in claim 1 wherein said power generator is an ultrasonic generator and wherein said operating parameter is one or more of an amplitude and a frequency of ultrasonic energy of said ultrasonic generator.

8. The tool of in claim 1 including an energy applicator coupled to said power generator and extending from said housing and wherein said energy applicator is one of an ultrasonic tip and a rotary bur.

9. The tool of in claim 1 wherein said magnet is a permanent magnet and wherein said sensors are Hall Effect sensors.

10. A method for operating a tool having a housing, a power generator disposed in the housing and having an operating parameter, a trigger member displaceable relative to the housing, a magnet coupled to the trigger member, a plurality of sensors located adjacent to the magnet and being disposed in the housing, and a controller coupled to the sensors, the method comprising the steps of:
- moving the magnet by displacing the trigger member;
- detecting the magnet with the sensors;
- generating an output signal from each sensor in response to detecting the magnet, wherein S is a total number of sensors that generate the output signals;
- receiving, with the controller, the output signal from each sensor;
- determining, with the controller, a base digital integer from each of the output signals, wherein the base digital integer is further defined as an N-bit digital integer, wherein N is a bit resolution of each sensor wherein the base digital integer is any one of $2^N$ values;
- concatenating, with the controller, the base digital integers to form a concatenated digital integer, wherein the concatenated digital integer is further defined as an M-bit digital integer, wherein M is a bit resolution of the concatenated digital integer with M=S*N and wherein the concatenated digital integer is any one of $2^M$ values; and
- varying, with the controller, the operating parameter based on a value of the concatenated digital integer.

11. The method of claim 10 wherein moving the magnet is further defined as moving the magnet along a predetermined path of movement.

12. The method of claim 10 wherein detecting the magnet further comprises detecting a magnetic field produced by the magnet with the magnetic field being variable as a function of a spatial relationship between the magnet and each sensor and wherein determining the base digital integer further comprises determining a strength of the magnetic field detected by each sensor.

13. The method of claim 10 wherein generating the output signal from each sensor further comprises generating an analog voltage signal from each sensor and wherein determining the base digital integer further comprises performing an analog-to-digital quantization of the analog voltage signal for each of the output signals.

14. The method of claim 10 further including the steps of:
- determining the base digital integer from each of the output signals after activating the tool and prior to trigger member displacement during which the trigger member has zero displacement;
- concatenating the base digital integers to establish a first concatenated digital integer corresponding to a minimum of an operating range of the operating parameter; and
- establishing a second concatenated digital integer by reversing the first concatenated digital integer wherein the second concatenated digital integer corresponds to an estimated maximum of the operating range of the operating parameter.

15. The method of claim 10 wherein the power generator is a motor and wherein varying the operating parameter further comprises varying one or more of a rotational speed and a rotational frequency of the motor.

16. The method of in claim 10 wherein the power generator is an ultrasonic generator and wherein varying the operating parameter further comprises varying one or more of an amplitude and a frequency of ultrasonic energy of the ultrasonic generator.

17. A method for controlling a surgical tool comprising a power generator, a displaceable magnet, a plurality of sensors located adjacent to the magnet, and with the surgical tool being coupled to a controller that is coupled to the sensors and the power generator, the method comprising the controller performing the steps of:
- receiving an output signal from each sensor in response to detecting the magnet, wherein S is a total number of sensors that generate the output signals;
- determining a base digital integer from each of the output signals, wherein the base digital integer is further defined as an N-bit digital integer, wherein N is a bit resolution of each sensor wherein the base digital integer is any one of $2^N$ values;
- concatenating the base digital integers to form a concatenated digital integer, wherein the concatenated digital integer is further defined as an M-bit digital integer, wherein M is a bit resolution of the concatenated digital integer with M=S*N and wherein the concatenated digital integer is any one of $2^M$ values; and
- varying operation of the power generator based on the concatenated digital integer.

* * * * *